(12) United States Patent
Peters et al.

(10) Patent No.: US 7,652,010 B2
(45) Date of Patent: Jan. 26, 2010

(54) AZABICYCLIC ARYL DERIVATIVES AND THEIR MEDICAL USE

(75) Inventors: Dan Peters, Balleup (DK); Daniel B. Timmermann, Ballerup (DK); Gunnar M. Olsen, Ballerup (DK); Elsebet Østergaard Nielsen, Ballerup (DK); Tino Dyhring Jørgensen, Ballerup (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 11/663,152

(22) PCT Filed: Oct. 14, 2005

(86) PCT No.: PCT/EP2005/055263

§ 371 (c)(1),
(2), (4) Date: Mar. 19, 2007

(87) PCT Pub. No.: WO2006/040352

PCT Pub. Date: Apr. 20, 2006

(65) Prior Publication Data

US 2007/0299082 A1    Dec. 27, 2007

(30) Foreign Application Priority Data

Oct. 15, 2004   (DK) .................. PA 2004 01582

(51) Int. Cl.
| | |
|---|---|
| A61K 31/35 | (2006.01) |
| A61K 31/501 | (2006.01) |
| A61K 31/53 | (2006.01) |
| A61K 31/497 | (2006.01) |
| A61K 31/506 | (2006.01) |
| C07D 401/04 | (2006.01) |
| C07D 498/08 | (2006.01) |
| C07D 513/08 | (2006.01) |
| C07D 515/08 | (2006.01) |
| C07D 401/12 | (2006.01) |
| C07D 403/12 | (2006.01) |
| C07D 405/12 | (2006.01) |
| A61K 43/66 | (2006.01) |
| A61P 29/00 | (2006.01) |
| C07D 453/02 | (2006.01) |

(52) U.S. Cl. ................ 514/252.04; 540/582; 544/238; 544/217; 544/218; 544/219; 544/298; 544/315; 544/316; 544/318; 544/319; 544/408; 544/409; 544/336; 514/214.03; 514/252.06; 546/137

(58) Field of Classification Search ............ 514/214.03, 514/252.04, 252.06; 540/582; 544/238
See application file for complete search history.

(56) References Cited

U.S. PATENT DOCUMENTS

| | | |
|---|---|---|
| 6,987,106 B1 | 1/2006 | Gallet et al. |
| 2002/0042428 A1 | 4/2002 | Myers et al. |
| 2006/0160877 A1 | 7/2006 | Luithle et al. |

FOREIGN PATENT DOCUMENTS

| | | | |
|---|---|---|---|
| WO | WO-00/58311 A | | 10/2000 |
| WO | WO-03/104227 A1 | | 12/2003 |
| WO | WO-2004/016617 A | | 2/2004 |
| WO | WO-2006/005608 A1 | | 1/2006 |
| WO | WO 2006005608 | * | 1/2006 |

OTHER PUBLICATIONS

Degroot, et al., Brain Research 949 (2002) 60-70.*
Tzavara, et al., The FASEB Journal express article 10.1096/fj.04-1575fje. Jul. 1, 2004.*
Parent, et al., Learn. & Mem. 2004, 11:9-20.*
Vallee, et al., Proc Natl Acad Sci, Dec. 23, 1997; 94(26): 14865-14870.*
Terry, et al., J. Pharmacol. & Experim. Therap., vol. 306, # 3, 821-827, Jun. 12, 2003.*
Potter, et al., Behav. Brain Res., vol. 175, # 2, Dec. 15, 2006, 201-211.*
Calabresi, et al., Trends in Neurosciences, vol. 23, # 3, Mar. 1, 2000, 120-126.*
Lippiello, et al., Expert Opinion on Drug Discovery, Sep. 2007, vol. 2, No. 9, pp. 1185-1203.*

* cited by examiner

Primary Examiner—Mark L Berch
Assistant Examiner—Cecilia M Jaisle
(74) Attorney, Agent, or Firm—Birch, Stewart, Kolasch & Birch, LLP

(57) ABSTRACT

Azabicyclo pyridazinyl compounds including azabicyclooctyl-pyridazinyl-oxy compounds, which are found to be cholinergic ligands at the nicotinic acetylcholine receptors and modulators of the monoamine receptors and transporters. Due to their pharmacological profile, the compounds may be used for the treatment of various diseases or disorders, including those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

17 Claims, No Drawings

AZABICYCLIC ARYL DERIVATIVES AND THEIR MEDICAL USE

TECHNICAL FIELD

This invention relates to novel azabicyclic aryl derivatives, which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency.

SUMMARY OF THE INVENTION

The present invention is devoted to the provision novel modulators of the nicotinic and/or of the monoamine receptors, which modulators are useful for the treatment of diseases or disorders related to the cholinergic receptors, and in particular the nicotinic acetylcholine receptor (nAChR), the serotonin receptor (5-HTR), the dopamine receptor (DAR) and the norepinephrine receptor (NER), and of the biogenic amine transporters for serotonin (5-HT), dopamine (DA) and norepinephrine (NE).

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides novel azabicyclic aryl derivatives of Formula I

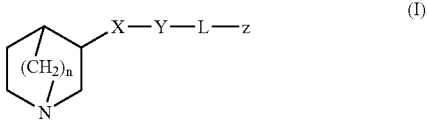

any of its enantiomers or any mixture of its enantiomers, or a pharmaceutically acceptable salt thereof, wherein n is 1, 2 or 3;

X represents O, S, NR', wherein R' represents hydrogen or alkyl;

Y represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro;

L represents a linking group selected from —CH$_2$—, —CH$_2$—CH$_2$—, —CH=CH—, and —C≡C—; and Z represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro.

In its second aspect the invention provides pharmaceutical compositions comprising a therapeutically effective amount of the azabicyclic aryl derivative of the invention, or a pharmaceutically-acceptable addition salt thereof, together with at least one pharmaceutically-acceptable carrier or diluent.

In a further aspect the invention relates to the use of the azabicyclic aryl derivative of the invention, or a pharmaceutically-acceptable addition salt thereof, for the manufacture of a pharmaceutical composition/medicament for the treatment, prevention or alleviation of a disease or a disorder or a condition of a mammal, including a human, which disease, disorder or condition is responsive to modulation of cholinergic receptors and/or monoamine receptors.

In a final aspect the invention provides methods of treatment, prevention or alleviation of diseases, disorders or conditions of a living animal body, including a human, which disorder, disease or condition is responsive to modulation of cholinergic receptors and/or monoamine receptors, which method comprises the step of administering to such a living animal body in need thereof a therapeutically effective amount of the azabicyclic aryl derivative of the invention.

Other objects of the invention will be apparent to the person skilled in the art from the following detailed description and examples.

DETAILED DISCLOSURE OF THE INVENTION

Azabicyclic Aryl Derivatives

In a first aspect novel azabicyclic aryl derivatives are provided. The azabicyclic aryl derivatives of the invention may be represented by the general Formula I

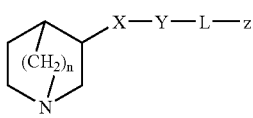

(I)

any of its enantiomers or any mixture of its enantiomers, or a pharmaceutically acceptable salt thereof, wherein n is 1, 2 or 3;

X represents O, S, NR', wherein R' represents hydrogen or alkyl;

Y represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro;

L represents a linking group selected from —CH$_2$—, —CH$_2$—CH$_2$—, —CH=CH—, and —C≡C—; and Z represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino and alkyl-carbonyl-amino.

In a preferred embodiment of the invention n is 1, 2 or 3.

In a more preferred embodiment n is 1 or 2.

In a most preferred embodiment n is 2.

In another preferred embodiment of the invention X represents O, S, NR', and wherein R' represents hydrogen or alkyl.

In a more preferred embodiment X represents O or S.

In a most preferred embodiment X represents O.

In a third preferred embodiment of the invention Y represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro.

In a more preferred embodiment Y represents an aromatic monocyclic or bicyclic heterocyclic group.

In an even more preferred embodiment Y represents a 5- or 6-membered monocyclic heterocyclic group selected from furanyl, thienyl, selenophenyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl and triazinyl.

In a yet more preferred embodiment Y represents a 5-membered monocyclic heterocyclic group selected from oxazolyl, in particular oxazol-2,4-diyl and oxazol-2,5-diyl; thiazolyl, in particular thiazol-2,4-diyl and thiazol-2,5-diyl; oxadiazolyl in particular 1,2,3-oxadiazol-4,5-diyl and 1,3,4-oxadiazol-2,5-diyl; and thiadiazolyl, in particular 1,2,3-thiadiazol-4,5-diyl and 1,3,4-thiadiazol-2,5-diyl.

In a most preferred embodiment Y represents thiazol-2,5-diyl, 1,3,4-oxadiazol-2,5-diyl or 1,3,4-thiadiazol-2,5-diyl.

In a another preferred embodiment Y represents a 6-membered monocyclic heterocyclic group selected from pyridyl, in particular pyrid-2,5-diyl, pyrid-2,6-diyl, pyrid-3,5-diyl and pyrid-3,6-diyl; pyridazinyl, in particular pyridazin-3,5-diyl and pyridazin-3,6-diyl; pyrimidinyl, in particular pyrimidin-2,5-diyl, pyrimidin-2,6-diyl and pyrimidin-4,6-diyl; and pyrazinyl, in particular pyrazin-2,5-diyl and pyridazin-2,6-diyl.

In a more preferred embodiment Y represents pyrid-2,5-diyl, pyridazin-3,6-diyl, pyrimidin-2,5-diyl or pyrazin-2,5-diyl.

In a most preferred embodiment Y represents pyridazin-3,6-diyl.

In a fourth preferred embodiment of the invention L represents —CH$_2$—, —CH$_2$—CH$_2$—, —CH=CH— or —C≡C—.

In a more preferred embodiment L represents —C≡C—.

In a fifth preferred embodiment of the invention Z represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino and alkyl-carbonyl-amino.

In a more preferred embodiment Z represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro.

In an even more preferred embodiment Z represents phenyl or naphthyl, which carbocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino and alkyl-carbonyl-amino.

In a yet more preferred embodiment Z represents phenyl, which carbocyclic group is optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino and alkyl-carbonyl-amino.

In a still more preferred embodiment Z represents phenyl or naphthyl, which carbocyclic group is optionally substituted with alkoxy, halo, trifluoromethyl, nitro, amino or alkyl-carbonyl-amino.

In a further still more preferred embodiment Z represents phenyl, which phenyl is optionally substituted one or two times with substituents selected from the group consisting of halo, alkoxy, trifluoromethyl, nitro, amino and alkyl-carbonyl-amino.

In a further still more preferred embodiment Z represents phenyl, which phenyl is optionally substituted with halo, alkoxy, amino or alkyl-carbonyl-amino.

In a further still more preferred embodiment Z represents phenyl.

In a further still more preferred embodiment Z represents a 5- or 6-membered monocyclic heterocyclic group selected from furanyl, thienyl, selenophenyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl and triazinyl, which heterocyclic group is optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino and alkyl-carbonyl-amino.

In a further still more preferred embodiment Z represents a 5-membered monocyclic heterocyclic group selected from furanyl, thienyl, oxazolyl, thiazolyl, imidazolyl, oxadiazolyl and thiadiazolyl, which heterocyclic group is optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino and alkyl-carbonyl-amino.

In a further still more preferred embodiment Z represents furanyl, thienyl or imidazolyl, which heterocyclic group is optionally substituted with halo, alkoxy, amino or alkyl-carbonyl-amino.

In a further still more preferred embodiment Z represents thienyl, which thienyl group is optionally substituted with halo, alkoxy, amino or alkyl-carbonyl-amino.

In a further still more preferred embodiment Z represents thienyl.

In a further still more preferred embodiment Z represents a 6-membered monocyclic heterocyclic group selected from pyridyl, pyrimidinyl and pyridazinyl, which heterocyclic group is optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino and alkyl-carbonyl-amino.

In a further still more preferred embodiment Z represents pyridyl, preferably pyridin-2-yl, pyridin-3-yl or pyridin-4-yl.

In a further still more preferred embodiment Z represents a bicyclic heterocyclic group selected from indolyl, benzofuranyl and benzothienyl, which bicyclic heterocyclic group is optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro.

In a further still more preferred embodiment Z represents indolyl, which is optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino and alkyl-carbonyl-amino.

In a further still more preferred embodiment Z represents indolyl.

In a further still more preferred embodiment Z represents phenyl or thienyl, which phenyl and thienyl groups are optionally substituted one or two times with substituents selected from the group consisting of halo, alkoxy, amino and alkyl-carbonyl-amino.

In a most preferred embodiment the azabicyclic aryl derivative of the invention is (±)-3-(6-Phenylethynyl-pyridazin-3-yloxy)-1-aza-bicyclo[2.2.2]octane;

(±)-3-[4-(3-Fluoro-phenylethynyl)-phenoxy]-1-aza-bicyclo[2.2.2]octane;

(±)-3-(4-Phenylethynyl-phenoxy)-1-aza-bicyclo[2.2.2]octane;

(±)-3-[4-(4-Methoxy-phenylethynyl)-phenoxy]-1-aza-bicyclo[0.2.2]octane;

(±)-3-[6-(4-Methoxy-phenylethynyl)-pyridazin-3-yloxy]-1-aza-bicyclo[2.2.2]octane;

(±)-N-{4-[6-(1-Aza-bicyclo[2.2.2]oct-3-yloxy)-pyridazin-3-ylethynyl]-phenyl}-acetamide;

(±)-3-[6-(1-Aza-bicyclo[2.2.2]oct-3-yloxy)-pyridazin-3-yl-ethynyl]-phenylamine;

(±)-4-[6-(1-Aza-bicyclo[2.2.2]oct-3-yloxy)-pyridazin-3-yl-ethynyl]-phenylamine;

(±)-N-{3-[6-(1-Aza-bicyclo[2.2.2]oct-3-yloxy)-pyridazin-3-ylethynyl]-phenyl}-acetamide;

(±)-3-(6-Thiophen-3-ylethynyl-pyridazin-3-yloxy)-1-aza-bicyclo[2.2.2]octane;

(±)-3-[6-(2-Fluoro-phenylethynyl)-pyridazin-3-yloxy]-1-aza-bicyclo[2.2.2]octane;

(±)-3-[6-(3-Fluoro-phenylethynyl)-pyridazin-3-yloxy]-1-aza-bicyclo[2.2.2]octane;

(±)-3-[6-(4-Fluoro-phenylethynyl)-pyridazin-3-yloxy]-1-aza-bicyclo[2.2.2]octane;

(±)-3-[6-(2,4-Difluoro-phenylethynyl)-pyridazin-3-yloxy]-1-aza-bicyclo[2.2.2]octane;

(±)-3-[6-(2-Nitro-phenylethynyl)-pyridazin-3-yloxy]-1-aza-bicyclo[2.2.2]octane;

(±)-3-[6-(3-Nitro-phenylethynyl)-pyridazin-3-yloxy]-1-aza-bicyclo[2.2.2]octane;

(±)-3-[6-(4-Nitro-phenylethynyl)-pyridazin-3-yloxy]-1-aza-bicyclo[2.2.2]octane;

(±)-3-[6-(2-Chloro-phenylethynyl)-pyridazin-3-yloxy]-1-aza-bicyclo[2.2.2]octane;

(±)-3-[6-(3-Chloro-phenylethynyl)-pyridazin-3-yloxy]-1-aza-bicyclo[2.2.2]octane;

(±)-3-[6-(4-Chloro-phenylethynyl)-pyridazin-3-yloxy]-1-aza-bicyclo[2.2.2]octane;

(±)-3-[6-(2-Trifluoromethyl-phenylethynyl)-pyridazin-3-yloxy]-1-aza-bicyclo[2.2.2]-octane;

(±)-3-[6-(3-Trifluoromethyl-phenylethynyl)-pyridazin-3-yloxy]-1-aza-bicyclo[2.2.2]-octane;

(±)-3-[6-(4-Trifluoromethyl-phenylethynyl)-pyridazin-3-yloxy]-1-aza-bicyclo[2.2.2]-octane;

(±)-3-[6-(3,5-Dimethoxy-phenylethynyl)-pyridazin-3-yloxy]-1-aza-bicyclo[2.2.2]-octane;

(±)-3-[6-(3,5-Difluoro-phenylethynyl)-pyridazin-3-yloxy]-1-aza-bicyclo[2.2.2]octane;

(±)-3-(6-Pyridin-2-ylethynyl-pyridazin-3-yloxy)-1-aza-bicyclo[2.2.2]octane;

(±)-3-(6-Pyridin-3-ylethynyl-pyridazin-3-yloxy)-1-aza-bicyclo[2.2.2]octane;

(±)-3-(6-Pyridin-4-ylethynyl-pyridazin-3-yloxy)-1-aza-bicyclo[2.2.2]octane;

(±)-3-[6-(6-Methoxy-naphthalen-2-ylethynyl)-pyridazin-3-yloxy]-1-aza-bicyclo[2.2.2]octane;

(±)-3-(6-Naphthalen-2-ylethynyl-pyridazin-3-yloxy)-1-aza-bicyclo[2.2.2]octane;

(±)-3-[6-(1H-Indol-5-ylethynyl)-pyridazin-3-yloxy]-1-aza-bicyclo[2.2.2]octane;

(±)-3-[6-(3-Methyl-3H-imidazol-4-ylethynyl)-pyridazin-3-yloxy]-1-aza-bicyclo[2.2.2]-octane;

(±)-N-{2-[6-(1-Aza-bicyclo[2.2.2]oct-3-yloxy)-pyridazin-3-ylethynyl]-phenyl}-acetamide; or (±)-2-[6-(1-Aza-bicyclo[2.2.2]oct-3-yloxy)-pyridazin-3-yl-ethynyl]-phenylamine;

or an enantiomer, or a mixture of its enantiomers, or a pharmaceutically acceptable salt thereof.

Any combination of two or more of the embodiments described herein is considered within the scope of the present invention.

Definition of Substituents

In the context of this invention halo represents a fluorine, a chlorine, a bromine or an iodine atom. Thus, a trihalomethyl group represents e.g. a trifluoromethyl group, a trichloromethyl group and similar trihalo-substituted methyl groups.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O-" group, wherein alkyl is as defined above. Examples of preferred alkoxy groups of the invention include methoxy and ethoxy.

In the context of this invention a cyanoalkyl group designates an "-alkyl-CN" group, wherein alkyl is as defined above.

In the context of this invention an alkyl-carbonyl-amino group designates an "alkyl-CO—NH—" group, wherein alkyl is as defined above. Preferred alkyl-carbonyl-amino groups of the invention include acetamido.

In the context of this invention an aromatic monocyclic or bicyclic carbocyclic group designates a monocyclic or polycyclic aromatic hydrocarbon group. Examples of preferred aryl groups of the invention include phenyl, indenyl, naphthyl, azulenyl, fluorenyl, and anthracenyl.

In the context of this invention an aromatic monocyclic or bicyclic heterocyclic group is a mono- or bicyclic compound, which holds one or more heteroatoms in its ring structure. The term "bi- and poly-heterocyclic groups" includes benzofused five- and six-membered heterocyclic rings containing one or more heteroatoms. Preferred heteroatoms include nitrogen (N), oxygen O, and sulphur (S).

In the context of this invention a 5-6 membered aromatic monocyclic heterocyclic designates a 5-6 membered heteroaryl, which holds one or more heteroatoms in its ring structure. Preferred heteroatoms include nitrogen (N), oxygen (O), and sulphur (S).

More preferred 5 membered heteroaryl groups of the invention include furanyl, in particular furan-2- or 3-yl; thienyl, in particular thien-2- or 3-yl; pyrrolyl (azolyl), in particular pyrrol-2- or 3-yl; oxazolyl, in particular oxazol-2, 4- or 5-yl; thiazolyl, in particular thiazol-2, 4- or 5-yl; isoxazolyl, in particular isoxazol-3, 4- or 5-yl; isothiazolyl, in particular isothiazol-3-, 4- or 5-yl; oxadiazolyl, in particular 1,2,3-oxadiazol-4- or 5-yl, or 1,3,4-oxadiazol-2-yl; and thiadiazolyl, in particular 1,2,3-thiadiazol-4- or 5-yl, or 1,3,4-thiadiazol-2-yl.

Most preferred 5 membered heteroaryl groups of the invention include furanyl, in particular furan-2- or 3-yl; and thienyl, in particular thien-2- or 3-yl.

More preferred 6 membered heteroaryl groups of the invention include pyridyl, in particular pyrid-2-, 3- or 4-yl; and pyrazinyl, in particular pyrazin-2- or 3-yl.

Preferred bicyclic heteroaryl groups of the invention include indolyl, in particular indol-2-, 5- or 6-yl; benzo[b]furanyl, in particular benzofuran-2-, 5- or 6-yl; benzo[b]thienyl, in particular benzothien-2-, 5- or 6-yl; and benzothiazolyl, in particular benzothiazol-2-, 5- or 6-yl.

Pharmaceutically Acceptable Salts

The azabicyclic aryl derivative of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydro-chloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound of the invention include alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Particularly preferred onium salts of the invention include those created at the N' position according to the following Formula I'

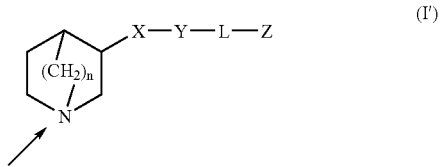

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Producing Azabicyclic Aryl Derivatives

The azabicyclic aryl derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention is devoted to the provision novel ligands and modulators of the nicotinic receptors, which ligands and modulators are useful for the treatment of diseases or disorders related to the cholinergic receptors, and in particular the nicotinic acetylcholine receptor (nAChR). Preferred compounds of the invention show a pronounced nicotinic acetylcholine $\alpha 7$ receptor subtype selectivity.

The compounds of the present invention may in particular be agonists, partial agonists, antagonists and/or allosteric modulators of the nicotinic acetylcholine receptor.

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compounds of the invention are used for the treatment of diseases, disorders, or conditions relating to the central nervous system. Such diseases or disorders includes anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In another preferred embodiment the compounds of the invention may be useful for the treatment of diseases, disorders, or conditions associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In yet another preferred embodiment the compounds of the invention may be useful for the treatment of endocrine disorders, such as thyrotoxicosis, pheochromocytoma, hypertension and arrhythmias.

In still another preferred embodiment the compounds of the invention may be useful for the treatment of neurodegenerative disorders, including transient anoxia and induced neuro-degeneration.

In even another preferred embodiment the compounds of the invention may be useful for the treatment of inflammatory diseases, disorders, or conditions, including inflammatory skin disorders such as acne and rosacea, Chron's disease, inflammatory bowel disease, ulcerative colitis, and diarrhoea.

In still another preferred embodiment the compounds of the invention may be useful for the treatment of mild, moderate or even severe pain of acute, chronic or recurrent character, as well as pain caused by migraine, postoperative pain, and phantom limb pain.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines and benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

Pharmaceutical Compositions

In another aspect the invention provides novel pharmaceutical compositions comprising a therapeutically effective amount of azabicyclic aryl derivative of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the azabicyclic aryl derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in drage, in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

The azabicyclic aryl derivatives of the present invention are valuable nicotinic and monoamine receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors and/or monoamine receptors, and which method comprises administering to such a living animal body, including a human, in need thereof an effective amount of an azabicyclic aryl derivative of the invention.

In a preferred embodiment, the disease, disorder or condition relates to the central nervous system.

In a preferred embodiment, the disease, disorder or condition is anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In a another preferred embodiment, the disease, disorder or condition are associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In a third preferred embodiment, the disease, disorder or condition is related to the endocrine system, such as thyrotoxicosis, pheochromocytoma, hypertension and arrhythmias.

In a fourth preferred embodiment, the disease, disorder or condition is a neurodegenerative disorders, including transient anoxia and induced neuro-degeneration.

In a fifth preferred embodiment, the disease, disorder or condition is an inflammatory disorder, including inflammatory skin disorders such as acne and rosacea, Chron's disease, inflammatory bowel disease, ulcerative colitis, and diarrhoea.

In a sixth preferred embodiment, the disease, disorder or condition is mild, moderate or even severe pain of acute, chronic or recurrent character, as well as pain caused by migraine, postoperative pain, and phantom limb pain.

In a seventh preferred embodiment, the disease, disorder or condition is associated with withdrawal symptoms caused by termination of use of addictive substances, including nicotine containing products such as tobacco, opioids such as heroin, cocaine and morphine, benzodiazepines and benzodiazepine-like drugs, and alcohol.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

EXAMPLES

The invention is further illustrated with reference to the following examples, which are not intended to be in any way limiting to the scope of the invention as claimed.

Example 1

Preparatory Example

All reactions involving air sensitive reagents or intermediates were performed under nitrogen and in anhydrous solvents. Magnesium sulphate was used as drying agent in the workup-procedures and solvents were evaporated under reduced pressure.

Method A (±)-3-(6-Bromo-pyridazin-3-yloxy)-1-aza-bicyclo[2.2.2]octane fumaric acid salt (Intermediate compound)

A mixture of (±)-3-quinuclidinol (3.0 g, 23.6 mmol) and 3,6-dibromopyridazine (5.61 g, 23.6 mmol) was solved in DMF (50 ml). Sodium hydride (60%; 1.9 g; 47.2 mmol) was added to the mixture at 0° C. over a 15 minutes time, followed by stirring at 0° C. for 45 minutes. The mixture was allowed to stir at room temperature over night. Aqueous sodium hydroxide (50 ml, 1M) was added. The mixture was extracted with diethylether (3×50 ml). Yield 2.0 g (30%). The corresponding salt was obtained by addition of a diethyl ether and methanol mixture (9:1) saturated with fumaric acid. Mp. 152.8° C.

(±)-3-(6-Iodo-pyridazin-3-yloxy)-1-aza-bicyclo[2.2.2]octane (Intermediate compound)

Was prepared according to method A. Mp. 156.3-158.8° C.

Method B (±)-3-(4-Iodo-phenoxy)-1-aza-bicyclo[2.2.2]octane (Intermediate compound)

Triphenylphosphine (37.1 g; 141.5 mmol) solved in dioxane (200 ml) was cooled to 10° C. Diethylazodicarboxylate (24.65 g; 141.5 mmol) was added to the mixture while the temperature was kept below 15° C. (±)3-Quinuclidinol (15.0 g; 117.93 mmol) and 4-iodophenol (28.5 g; 129.7 mmol) was added to the mixture The mixture was stirred at room temperature for 15 hours. Aqueous sodium hydroxide (200 ml; 1 M) was added and the dioxane was evaporated. The mixture was extracted with dichlorometane (2×200 ml), the organic phase was dried and evaporated. Diethylether (150 ml) was added and triphenylphosphine oxide was filtered off. The ether phase was washed with water (100 ml). The organic phase was dried and evaporated followed by column chromatography using a mixture of dichloromethane: methanol (9:1) and aqueous ammonia (1%). The title compound was isolated 8.76 g (23%).

Method C (±)-3-(6-Phenylethynyl-pyridazin-3-yloxy)-1-aza-bicyclo[2.2.2]octane fumaric acid salt (Compound C1)

A mixture of (±)-3-(6-bromo-pyridazin-3-yloxy)-1-aza-bicyclo[2.2.2]octane (1.71 g; 6.0 mmol), phenylacetylene (1.3 ml; 12 mmol), palladacycle (113 mg; 0.12 mmol), CuI (114 mg; 0.60 mmol), diisopropylethylamine (1.0 ml; 6.0 mmol) and dioxane (20 ml) was stirred for 15 hours at 100° C. Aqueous sodium hydroxide (50 ml; 1M) was added. The mixture was extracted with dichloromethane (3×30 ml). Chromatography on silica gel with dichloromethane, methanol and conc. ammonia (89:10:1) gave the title compound as an oil. Yield 0.35 g (19%).

The corresponding salt was obtained by addition of a diethyl ether and methanol mixture (9:1) saturated with fumaric acid. Mp. 198-202° C.

(±)-3-[4-(3-Fluoro-phenylethynyl)-phenoxy]-1-aza-bicyclo[2.2.2]octane free base (Compound C2)

Was prepared according to method C from (±)-3-(4-iodo-phenoxy)-1-aza-bicyclo[2.2.2]octane. Mp. 186.3-186.7° C.

(±)-3-(4-Phenylethynyl-phenoxy)-1-aza-bicyclo[2.2.2]octane fumaric acid salt (Compound C3)

Was prepared according to method C from (±)-3-(4-iodo-phenoxy)-1-aza-bicyclo[2.2.2]octane. Mp. 126.9-127.3° C.

(±)-3-[4-(4-Methoxy-phenylethynyl)-phenoxy]-1-aza-bicyclo[2.2.2]octane free base (Compound C4)

Was prepared according to method C from (±)-3-(4-iodo-phenoxy)-1-aza-bicyclo[2.2.2]octane. Mp. 112-115° C.

(±)-3-[6-(4-Methoxy-phenylethynyl)-pyridazin-3-yloxy]-1-aza-bicyclo[2.2.2]octane free base (Compound C5)

Was prepared according to method C from (±)-3-(6-iodo-pyridazin-3-yloxy)-1-aza-bicyclo[2.2.2]octane. Mp. 162.9-164.7° C.

(±)-N-{4-[6-(1-Aza-bicyclo[2.2.2]oct-3-yloxy)-pyridazin-3-ylethynyl]-phenyl}-acetamide free base (Compound C6)

Was prepared according to method C from (±)-3-(6-iodo-pyridazin-3-yloxy)-1-aza-bicyclo[2.2.2]octane. Mp. 169.5-175.4° C.

(±)-3-[6-(1-Aza-bicyclo[2.2.2]oct-3-yloxy)-pyridazin-3-ylethynyl]-phenylamine free base (Compound C7)

Was prepared according to method C from (±)-3-(6-iodo-pyridazin-3-yloxy)-1-aza-bicyclo[2.2.2]octane. Mp. 152.4-158.1° C.

(±)-4-[6-(1-Aza-bicyclo[2.2.2]oct-3-yloxy)-pyridazin-3-ylethynyl]-phenylamine free base (Compound C8)

Was prepared according to method C from (±)-3-(6-iodo-pyridazin-3-yloxy)-1-aza-bicyclo[2.2.2]octane. Mp. 212-220° C.

(±)-N-{3-[6-(1-Aza-bicyclo[2.2.2]oct-3-yloxy)-pyridazin-3-ylethynyl]-phenyl}-acetamide free base (Compound C9)

Was prepared according to method C from (±)-3-(6-iodo-pyridazin-3-yloxy)-1-aza-bicyclo[2.2.2]octane. Mp. 131.9-133.8° C.

(±)-3-(6-Thiophen-3-ylethynyl-pyridazin-3-yloxy)-1-aza-bicyclo[2.2.2]octane fumaric acid salt (Compound C10)

Was prepared according to method C from (±)-3-(6-iodo-pyridazin-3-yloxy)-1-aza-bicyclo[2.2.2]octane. Mp. 133.9-141.6° C.

The following compounds are prepared according to Method C:
(±)-3-[6-(2-Fluoro-phenylethynyl)-pyridazin-3-yloxy]-1-aza-bicyclo[2.2.2]-octane (Compound C11);
(±)-3-[6-(3-Fluoro-phenylethynyl)-pyridazin-3-yloxy]-1-aza-bicyclo[2.2.2]-octane (Compound C12);
(±)-3-[6-(4-Fluoro-phenylethynyl)-pyridazin-3-yloxy]-1-aza-bicyclo[2.2.2]-octane (Compound C13);
(±)-3-[6-(2,4-Difluoro-phenylethynyl)-pyridazin-3-yloxy]-1-aza-bicyclo[2.2.2]-octane (Compound C14);
(±)-3-[6-(2-Nitro-phenylethynyl)-pyridazin-3-yloxy]-1-aza-bicyclo[2.2.2]-octane (Compound C15);
(±)-3-[6-(3-Nitro-phenylethynyl)-pyridazin-3-yloxy]-1-aza-bicyclo[2.2.2]-octane (Compound C16);
(±)-3-[6-(4-Nitro-phenylethynyl)-pyridazin-3-yloxy]-1-aza-bicyclo[2.2.2]-octane (Compound C17);
(±)-3-[6-(2-Chloro-phenylethynyl)-pyridazin-3-yloxy]-1-aza-bicyclo[2.2.2]-octane (Compound C18);
(±)-3-[6-(3-Chloro-phenylethynyl)-pyridazin-3-yloxy]-1-aza-bicyclo[2.2.2]-octane (Compound C19);
(±)-3-[6-(4-Chloro-phenylethynyl)-pyridazin-3-yloxy]-1-aza-bicyclo[2.2.2]-octane (Compound C20);
(±)-3-[6-(2-Trifluoromethyl-phenylethynyl)-pyridazin-3-yloxy]-1-aza-bicyclo-[2.2.2]octane (Compound C21);
(±)-3-[6-(3-Trifluoromethyl-phenylethynyl)-pyridazin-3-yloxy]-1-aza-bicyclo-[2.2.2]octane (Compound C22);
(±)-3-[6-(4-Trifluoromethyl-phenylethynyl)-pyridazin-3-yloxy]-1-aza-bicyclo-[2.2.2]octane (Compound C23);
(±)-3-[6-(3,5-Dimethoxy-phenylethynyl)-pyridazin-3-yloxy]-1-aza-bicyclo-[2.2.2]octane (Compound C24);
(±)-3-[6-(3,5-Difluoro-phenylethynyl)-pyridazin-3-yloxy]-1-aza-bicyclo[2.2.2]-octane (Compound C25);
(±)-3-(6-Pyridin-2-ylethynyl-pyridazin-3-yloxy)-1-aza-bicyclo[2.2.2]octane (Compound C26);
(±)-3-(6-Pyridin-3-ylethynyl-pyridazin-3-yloxy)-1-aza-bicyclo[2.2.2]octane (Compound C27);

(±)-3-(6-Pyridin-4-ylethynyl-pyridazin-3-yloxy)-1-aza-bicyclo[2.2.2]octane (Compound C28);

(±)-3-[6-(6-Methoxy-naphthalen-2-ylethynyl)-pyridazin-3-yloxy]-1-aza-bicyclo[2.2.2]octane (Compound C29);

(±)-3-(6-Naphthalen-2-ylethynyl-pyridazin-3-yloxy)-1-azabicyclo[2.2.2]-octane (Compound C30);

(±)-3-[6-(1H-Indol-5-ylethynyl)-pyridazin-3-yloxy]-1-azabicyclo[2.2.2]octane (Compound C31);

(±)-3-[6-(3-Methyl-3H-imidazol-4-ylethynyl)-pyridazin-3-yloxy]-1-aza-bicyclo[2.2.2]octane (Compound C32);

(±)-N-{2-[6-(1-Aza-bicyclo[2.2.2]oct-3-yloxy)-pyridazin-3-ylethynyl]-phenyl}-acetamide (Compound C33); and (±)-2-[6-(1-Aza-bicyclo[2.2.2]oct-3-yloxy)-pyridazin-3-yl-ethynyl]-phenylamine (Compound C34).

Example 2

In vitro Inhibition of $^3$H-α-Bungarotoxine Binding in Rat Brain

In this example the affinity of the compounds of the invention for binding to $α_7$-subtype of nicotinic receptors is determined.

α-Bungarotoxine is a peptide isolated from the venom of the Elapidae snake *Bungarus multicinctus*. It has high affinity for neuronal and neuromuscular nicotinic receptors, where it acts as a potent antagonist.

$^3$H-α-Bungarotoxine labels nicotinic acetylcholine receptors formed by the $α_7$ subunit isoform found in brain and the $α_1$ isoform in the neuromuscular junction.

Tissue Preparation

Preparations are performed at 0-4° C. Cerebral cortices from male Wistar rats (150-250 g) are homogenised for 10 seconds in 15 ml of 20 mM Hepes buffer containing 118 mM NaCl, 4.8 mM KCl, 1.2 mM MgSO$_4$ and 2.5 mM CaCl$_2$ (pH 7.5) using an Ultra-Turrax homogeniser. The tissue suspension is subjected to centrifugation at 27,000×g for 10 minutes. The supernatant is discarded and the pellet is washed twice by centrifugation at 27,000×g for 10 minutes in 20 ml of fresh buffer, and the final pellet is then re-suspended in fresh buffer containing 0.01% BSA (35 ml per g of original tissue) and used for binding assays.

Assay

Aliquots of 500 µl of homogenate are added to 25 µl of test solution and 25 µl of $^3$H-α-bungarotoxine (2 nM, final concentration) and mixed and incubated for 2 hours at 37° C. Non-specific binding is determined using (−)-nicotine (1 mM, final concentration). After incubation, the samples are added 5 ml of ice-cold Hepes buffer containing 0.05% PEI and poured directly onto Whatman GF/C glass fibre filters (pre-soaked in 0.1% PEI for at least 6 hours) under suction, and immediately washed with 2×5 ml ice-cold buffer.

The amount of radioactivity on the filters is determined by conventional liquid scintillation counting. Specific binding is total binding minus non-specific binding.

The test value is given as an IC$_{50}$ (the concentration of the test substance which inhibits the specific binding of $^3$H-α-bungarotoxin by 50%).

Initially compounds C1, C6, C7, C8 and C10 were subjected to this assay and they all showed results at the sub-micro-molar (<1 µM) level.

The invention claimed is:

1. An azabicyclic pyridazinyl compound represented by Formula I

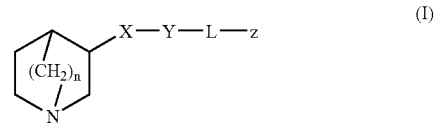

any of its enantiomers or any mixture of its enantiomers, or a pharmaceutically acceptable salt thereof, wherein n is 1, 2 or 3;

X represents O, S, NR', wherein R' represents hydrogen or alkyl;

Y represents a pyridazinyl group;

L represents a linking group selected from —CH$_2$—, —CH$_2$—CH$_2$—, —CH═CH—, and —C≡C—; and Z represents an aromatic monocyclic or bicyclic carbocyclic or heterocyclic group selected from phenyl, naphthyl, thienyl, pyridyl, imidazolyl, and indolyl, which phenyl, naphthyl, thienyl, pyridyl, imidazolyl, and indolyl groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino and alkyl-carbonyl-amino.

2. The azabicyclic pyridazinyl compound of claim 1, wherein n is 1 or 2.

3. The azabicyclic pyridazinyl compound of claim 2, wherein n is 2.

4. The azabicyclic pyridazinyl compound of claim 1, wherein X represents O or S.

5. The azabicyclic pyridazinyl compound of claim 4, wherein X represents O.

6. The azabicyclic pyridazinyl compound of claim 1, wherein L represents —CH═CH— or —C≡C—.

7. The azabicyclic pyridazinyl compound of claim 6, wherein L represents —C≡C—.

8. The azabicyclic pyridazinyl compound of claim 1, wherein Z represents phenyl or naphthyl, which carbocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino and alkyl-carbonyl-amino.

9. The azabicyclic pyridazinyl compound of claim 8, wherein Z represents phenyl, which carbocyclic group is optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino and alkyl-carbonyl-amino.

10. The azabicyclic pyridazinyl compound of claim 9, wherein Z represents phenyl.

11. The azabicyclic pyridazinyl compound of claim 1, wherein Z represents a 5- or 6-membered monocyclic heterocyclic group selected from thienyl, imidazolyl, and pyridyl, which heterocyclic group is optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino and alkyl-carbonyl-amino.

12. The azabicyclic pyridazinyl compound of claim 11, wherein Z represents a 5-membered monocyclic heterocyclic group selected from thienyl and imidazolyl, which heterocyclic group is optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino and alkyl-carbonyl-amino.

13. The azabicyclic pyridazinyl compound of claim 11, wherein Z represents pyridyl, optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino and alkyl-carbonyl-amino.

14. The azabicyclic pyridazinyl compound of claim 1, wherein Z represents indolyl, optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino and alkyl-carbonyl-amino.

15. The azabicyclic pyridazinyl compound of claim 1, wherein Z represents phenyl or thienyl, which phenyl and thienyl groups are optionally substituted one or two times with substituents selected from the group consisting of halo, alkoxy, amino and alkyl-carbonyl-amino.

16. The azabicyclic pyridazinyl compound of claim 1, which is (±)-3-(6-Phenylethynyl-pyridazin-3-yloxy)-1-aza-bicyclo [2.2.2]octane;
(±)-3-[6-(4-Methoxy-phenylethynyl)-pyridazin-3-yloxy]-1-aza-bicyclo[2.2.2]octane;
(±)-N-{4-[6-(1-Aza-bicyclo[2.2.2]oct-3-yloxy)-pyridazin-3-ylethynyl]-phenyl}-acetamide;
(±)-3-[6-(1-Aza-bicyclo[2.2.2]oct-3-yloxy)-pyridazin-3-ylethynyl]-phenylamine;
(±)-4-[6-(1-Aza-bicyclo[2.2.2]oct-3-yloxy)-pyridazin-3-ylethynyl]-phenylamine;
(±)-N-{3-[6-(1-Aza-bicyclo[2.2.2]oct-3-yloxy)-pyridazin-3-ylethynyl]-phenyl}-acetamide;
(±)-3-(6-Thiophen-3-ylethynyl-pyridazin-3-yloxy)-1-aza-bicyclo [2.2.2]octane;
(±)-3-[6-(2-Fluoro-phenylethynyl)-pyridazin-3-yloxy]-1-aza-bicyclo [2.2.2]octane;
(±)-3-[6-(3-Fluoro-phenylethynyl)-pyridazin-3-yloxy]-1-aza-bicyclo [2.2.2]octane;
(±)-3-[6-(4-Fluoro-phenylethynyl)-pyridazin-3-yloxy]-1-aza-bicyclo [2.2.2]octane;
(±)-3-[6-(2,4-Difluoro-phenylethynyl)-pyridazin-3-yloxy]-1-aza-bicyclo[2.2.2]octane;
(±)-3-[6-(2-Nitro-phenylethynyl)-pyridazin-3-yloxy]-1-aza-bicyclo [2.2.2]octane;
(±)-3-[6-(3-Nitro-phenylethynyl)-pyridazin-3-yloxy]-1-aza-bicyclo [2.2.2]octane;
(±)-3-[6-(4-Nitro-phenylethynyl)-pyridazin-3-yloxy]-1-aza-bicyclo [2.2.2]octane;
(±)-3-[6-(2-Chloro-phenylethynyl)-pyridazin-3-yloxy]-1-aza-bicyclo [2.2.2]octane;
(±)-3-[6-(3-Chloro-phenylethynyl)-pyridazin-3-yloxy]-1-aza-bicyclo [2.2.2]octane;
(±)-3-[6-(4-Chloro-phenylethynyl)-pyridazin-3-yloxy]-1-aza-bicyclo [2.2.2]octane;
(±)-3-[6-(2-Trifluoromethyl-phenylethynyl)-pyridazin-3-yloxy]-1-aza-bicyclo[2.2.2]octane;
(±)-3-[6-(3-Trifluoromethyl-phenylethynyl)-pyridazin-3-yloxy]-1-aza-bicyclo[2.2.2]octane;
(±)-3-[6-(4-Trifluoromethyl-phenylethynyl)-pyridazin-3-yloxy]-1-aza-bicyclo[2.2.2]octane;
(±)-3[6-(3,5-Dimethoxy-phenylethynyl)-pyridazin-3-yloxy]-1-aza-bicyclo[2.2.2]octane;
(±)-3-[6-(3,5-Difluoro-phenylethynyl)-pyridazin-3-yloxy]-1-aza-bicyclo[2.2.2]octane;
(±)-3-(6-Pyridin-2-ylethynyl-pyridazin-3-yloxy)-1-aza-bicyclo[2.2.2]octane;
(±)-3-(6-Pyridin-3-ylethynyl-pyridazin-3-yloxy)-1-aza-bicyclo[2.2.2]octane;
(±)-3-(6-Pyridin-4-ylethynyl-pyridazin-3-yloxy)-1-aza-bicyclo[2.2.2]octane;
(±)-3-[6-(6-Methoxy-naphthalen-2-ylethynyl)-pyridazin-3-yloxy]-1-aza-bicyclo[2.2.2]-octane;
(±)-3-(6-Naphthalen-2-ylethynyl-pyridazin-3-yloxy)-1-aza-bicyclo[2.2.2]octane;
(±)-3-[6-(1H-Indol-5-ylethynyl)-pyridazin-3-yloxy]-1-aza-bicyclo[2.2.2]octane;
(±)-3-[6-(3-Methyl-3H-imidazol-4-ylethynyl)-pyridazin-3-yloxy]-1-aza-bicyclo[2.2.2]-octane;
(±)-N-{2-[6-(1-Aza-bicyclo[2.2.2]oct-3-yloxy)-pyridazin-3-ylethynyl]-phenyl}-acetamide; or
(±)-2-[6-(1-Aza-bicyclo[2.2.2]oct-3-yloxy)-pyridazin-3-ylethynyl]-phenylamine;
or an enantiomer, or a mixture of its enantiomers, or a pharmaceutically acceptable salt thereof.

17. A pharmaceutical composition comprising a therapeutically effective amount of an azabicyclic pyridazinyl compound of claim 1, or a pharmaceutically-acceptable addition salt thereof, together with at least one pharmaceutically-acceptable carrier or diluent.

* * * * *